United States Patent
Bowman

(10) Patent No.: US 6,179,840 B1
(45) Date of Patent: Jan. 30, 2001

(54) GRAFT FIXATION DEVICE AND METHOD

(75) Inventor: Steven M. Bowman, Sherborn, MA (US)

(73) Assignee: Ethicon, Inc., Somerville, NJ (US)

(*) Notice: Under 35 U.S.C. 154(b), the term of this patent shall be extended for 0 days.

(21) Appl. No.: 09/360,367

(22) Filed: Jul. 23, 1999

(51) Int. Cl.[7] .................................................... A61F 5/04
(52) U.S. Cl. ................................ 606/72; 606/75; 606/73; 606/220; 128/899
(58) Field of Search ........................... 606/75, 72, 219, 606/220, 218, 216, 221, 139, 142; 128/899

(56) References Cited

U.S. PATENT DOCUMENTS

| | | | |
|---|---|---|---|
| 4,454,875 | * | 6/1984 | Pratt et al. ................................ 606/72 |
| 4,548,202 | | 10/1985 | Duncan . |
| 5,269,783 | | 12/1993 | Sander . |
| 5,352,229 | | 10/1994 | Goble et al. . |
| 5,454,814 | * | 10/1995 | Comte ...................................... 606/75 |
| 5,500,000 | | 3/1996 | Feagin et al. . |
| 5,520,700 | | 5/1996 | Beyar et al. . |
| 5,569,252 | | 10/1996 | Justin et al. . |
| 5,643,319 | * | 7/1997 | Green et al. .......................... 606/218 |
| 5,647,874 | | 7/1997 | Hayhurst . |
| 5,656,492 | | 8/1997 | Glowacki et al. . |
| 5,658,313 | | 8/1997 | Thal . |
| 5,702,462 | * | 12/1997 | Oberlander .......................... 606/220 |

FOREIGN PATENT DOCUMENTS 0 578 425 B1   9/1997   (EP) .............................. A61B/17/064

OTHER PUBLICATIONS

Bonding of Cartilage Matrices with Cultured Chondrocytes: An Experimental Model Authors: Giuseppe M. Peretti, Mark A Randolph, Enzo M. Caruso, Francesco Rossetti and David J. Zaleske, (Reprinted from The Journal of Orthopaedic Research, vol. 6, No. 1, pp 89–95, Jan. 1998).

* cited by examiner

*Primary Examiner*—Pedro Philogene

(57) ABSTRACT

A graft fixation device. The device is useful for affixing a tissue graft to a bone or other body surface. The graft fixation device comprises two implantation members connected by a connecting member. The implantation members have longitudinal passageways therethrough.

9 Claims, 11 Drawing Sheets

GRAFT FIXATION DEVICE AND METHOD

TECHNICAL FIELD

The field of art to which this invention relates is surgical fastening devices, in particular, surgical fastening devices for fixating tissue grafts to bone.

BACKGROUND OF THE INVENTION

The medical technology associated with tissue engineering has advanced at a rapid pace. In particular, it is now known to harvest cells from the human body, for example, chondrocytes and fibrochrondrocytes from the knee joint. These autologous cells are then cultured in a laboratory environment on a bioabsorbable matrix. The matrix will typically have a shape substantially similar to the tissue section which needs to be replaced. After a sufficient period of time in an appropriate culture medium at the proper environmental conditions, the harvested cells will grow on the matrix to form an implantable section of tissue having substantially the same physical configuration as the section of tissue which needs to be replaced in the patient. Such a tissue-engineered construct consisting of cells on the matrix (or, alternatively, consisting of a matrix alone without cells) is then affixed to the bone site using conventionally known surgical fasteners including sutures, periosteal coverings, or fibrin glue.

The advantages of tissue engineering are many, not the least of which is, for example, that it is now possible to replace cartilage with living cartilage tissue. In addition, the likelihood of rejection of the tissue implant is minimized since the cartilage tissue which has been grown in-vitro is identical to the autologous cartilage of the patient.

Although existing matrix fixation devices are adequate for their intended use, there are also some disadvantages attendant with their use. First of all these fixation devices are generic in the sense that they are not specifically designed for matrix fixation to bone or soft tissue, but can be used for a variety of surgical procedures. Other disadvantages include the difficulty in using many of these devices in a minimally invasive arthroscopic procedure. Additional disadvantages include the difficulty and surgical challenge of harvesting a piece of periosteum for use as a periosteal flap, the significant patient morbidity associated with such harvesting, and the difficulty in suturing such a thin, compliant material to surrounding tissue.

Accordingly, there is a need in this art for novel fixation devices that will effectively affix a matrix of tissue-engineered tissue to a bone or other anchoring site so that the tissue may continue to grow and regenerate in the patient's body.

DISCLOSURE OF THE INVENTION

Therefore, it is an object of the present invention to provide a fixation device that effectively fixates a tissue-engineered matrix to a bone or other anchoring site, thereby enabling the implanted matrix to remain in place while the tissue continues to grow and regenerate.

It is a further object of the present invention to provide such a device for fixating a matrix to a bone site which is easily installed using an arthroscopic procedure or an open procedure.

It is yet a further object of the present invention to provide such a device for fixating a matrix to a bone site which does not require sutures or suture knot tying.

It is still yet a further object of the present invention to provide a surgical method for fixating a matrix utilizing such a device in a location within a patient's body.

Accordingly, a graft fixation device is disclosed. The graft fixation device has first and second implantation members. The members are elongated and preferably have a cylindrical configuration. The members also have distal ends, proximal ends, and longitudinal axes. There are longitudinal passages extending through the entire length of each implantation member. The members have outer surfaces. The implantation members are connected to each other by a rod member having first and second ends and a central section. The first end of the rod member extends from the proximal end of the first implantation member and the second end of the rod member extends from the proximal end of the second implantation member. The rod member is preferably relatively rigid and may be configured to have geometric shape, for example, an inverted "U" shape. However, the rod member may also be flexible. The rod member maintains the implantation members at a relatively fixed distance from each other. The central section of the rod member is designed to engage a section of a tissue-engineered matrix implant. In a preferred embodiment, the implantation members have a series of ridges extending out from the outer surfaces of the implantation members to assist in preventing withdrawal from a bone site or other anchoring site after the implantation members are implanted into previously-created bore holes.

Yet another aspect of the present invention is a method of using the graft fixation device of the present invention to affix a matrix containing tissue-engineered tissue to a bone.

These and other features and advantages of the present invention will become more apparent from the following description and accompanying drawings.

DESCRIPTION OF THE PREFERRED EMBODIMENTS

The graft fixation devices of the present invention can be made from conventional bio-compatible materials, including absorbable and non-absorbable materials, as well as biodegradable materials. The non-absorbable materials which can be utilized include conventional biocompatible materials such as stainless steel, polyethylene, Teflon, Nitinol, non-absorbable polymers, other bio-compatible metals, ceramics, combinations thereof and the like. The absorbable materials which can be used to manufacture the graft fixation devices of the present invention will typically include those conventional bioabsorbable or bioresorbable materials known in this art which can be effectively molded or machined. The bio-absorbable and bio-resorbable materials include polylactic acid, polydioxanone, polycaprolactone, polyglycolic acid, polygalactic acid, other known biocompatible bioabsorbable and bioresorbable polymers, ceramics, composites, combinations thereof and the like and equivalents thereof.

Figure 1:
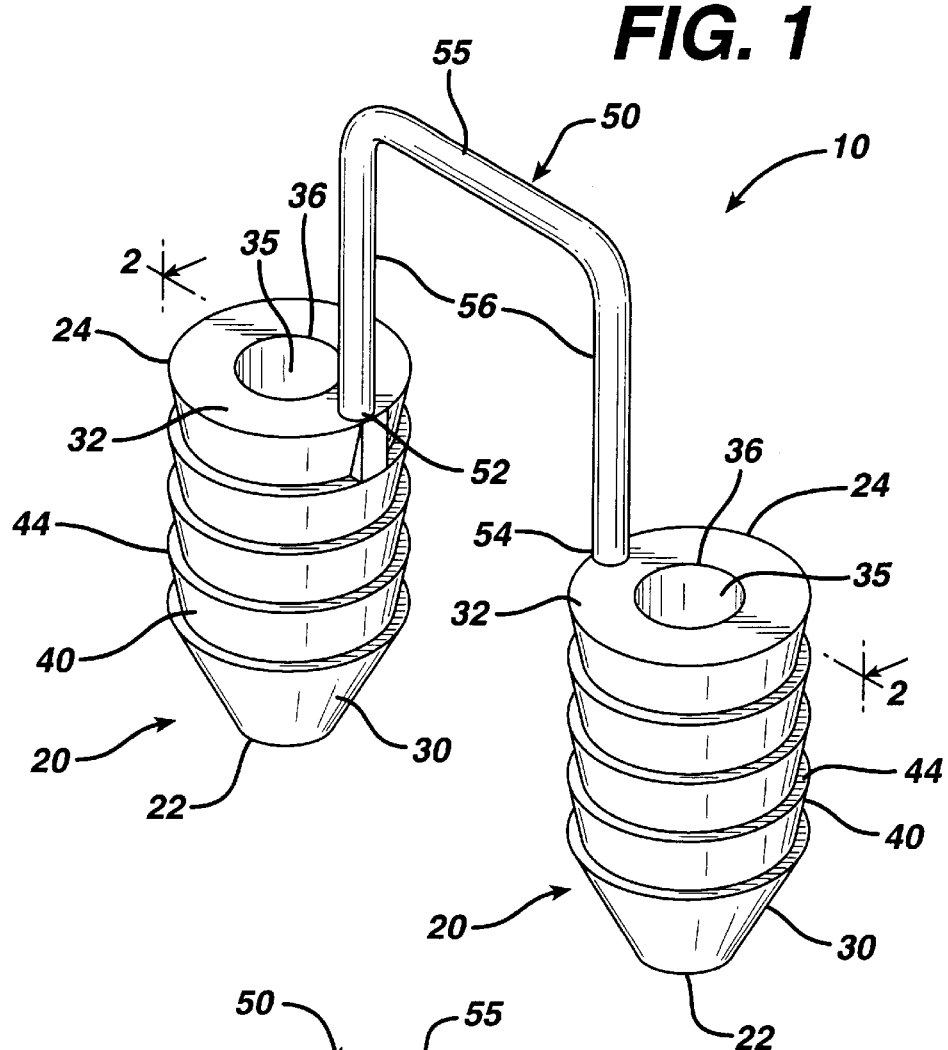
FIG. 1 is a perspective view of a graft fixation device of the present invention.
Figure 2:
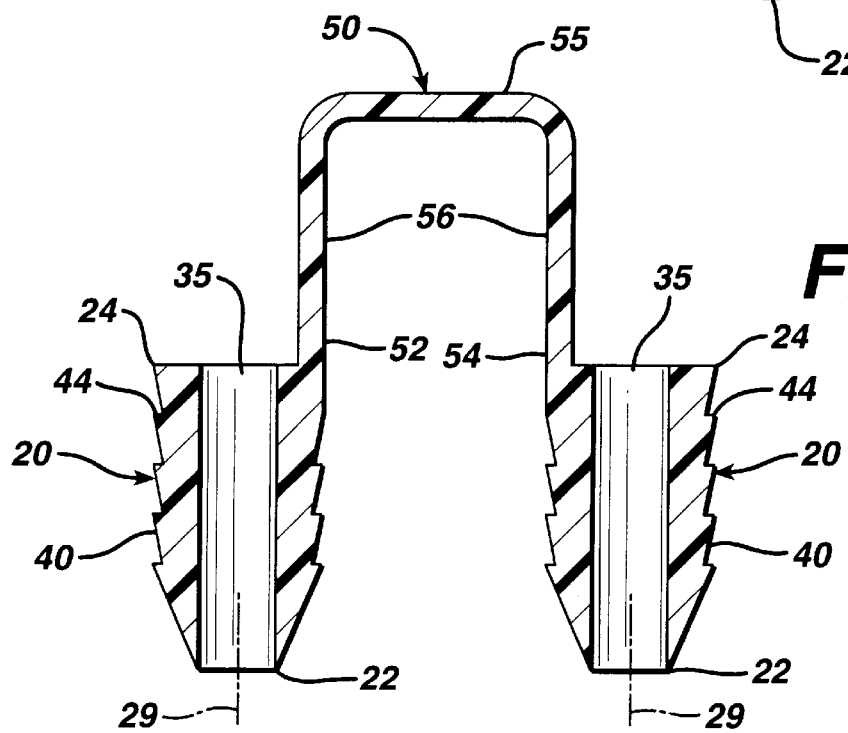
FIG. 2 is a cross-sectional view of the graft fixation device of FIG. 1 taken along view line 2—2.

Referring now to FIGS. 1–2, a preferred embodiment of a graft fixation device 10 of the present invention is illustrated. The graft fixation device 10 is seen to have implantation members 20. The implantation members 20 are seen to be elongated members, preferably having a substantially cylindrical shape. The members 20 may have other geometric shapes including conical, pyramidal, polygonal, cubic, spherical, etc. The implantation members 20 are seen to have distal ends 22 and proximal ends 24. Each implantation member 20 is seen to have an outer surface 28 and a longitudinal axis 29. Each member 20 is also seen to have longitudinal passage 35 extending therethrough. The implantation members 20 are also seen to have optional frustoconical ends 30, and proximal endface surfaces 32. Although it is preferred that endface surfaces 32 be flat, endface surface 32 may also be angled, concave, convex, etc. Endface surface 32 is seen to have central circular opening 36 in communication with passage 35. Preferably, central opening 36 will have a circular cross-section, but it may have other geometric cross-sections as well including elliptical, polygonal, square, rectangular, combinations thereof and the like. Members 20 are also seen to have distal end face surfaces 37 having circular openings 38 in communication with passages 35. As shown with the optional frustoconical end 30, the annular end face surface 37 is of de minimis thickness around opening 38, however this thickness would increase in the absence of a frustoconical end. Also seen to extend out from the surface 28 of member 20 are a series of optional projections 40 having tissue engagement edges 44. Without the projections 40, the surface 28 of the member 20 will be smooth.

The device 10 is seen to have graft retention member 50 connecting the implantation members 20. Retention member 50 is seen to be a rod-like member having first end 52, second end 54 and central section 55. First end 52 is seen to extend from proximal endface surface 32 of the first member 20 while end 54 is seen to extend up from the proximal endface surface 32 of the other member 20. The ends 54 and 52 of retention member 50 may also if desired extend from or be mounted to any section of outer surface 28. The connecting member 50 is seen to be preferably bent or shaped into three segments including top segment 55 and leg segments 56. The top segment 55 is seen to be substantially perpendicular to the leg segments 56. Although it is preferred that connecting member 50 have an inverted "U" configuration, the connecting member 50 may have other geometric configurations including semicircular, arced, curved, triangular, polygonal, U-shaped, and the like and combinations thereof. The ends 52 and 54 of connecting member 50 may be permanently affixed to the implantation members 20, or may be removably attached thereto in a conventional manner. Member 50 may be rigid or flexible. Member 50 will have a sufficient surface area to effectively retain a tissue-engineered matrix in place on a bone or other body surface. Preferably, connecting member 50 will have a circular cross-section, but may have other geometric cross-sections as well including elliptical, polygonal, square, rectangular, combinations thereof and the like. Member 50 may be rigid or flexible, and may have a single filamentary structure or have multiple interconnected filaments or members.

Figure 3:
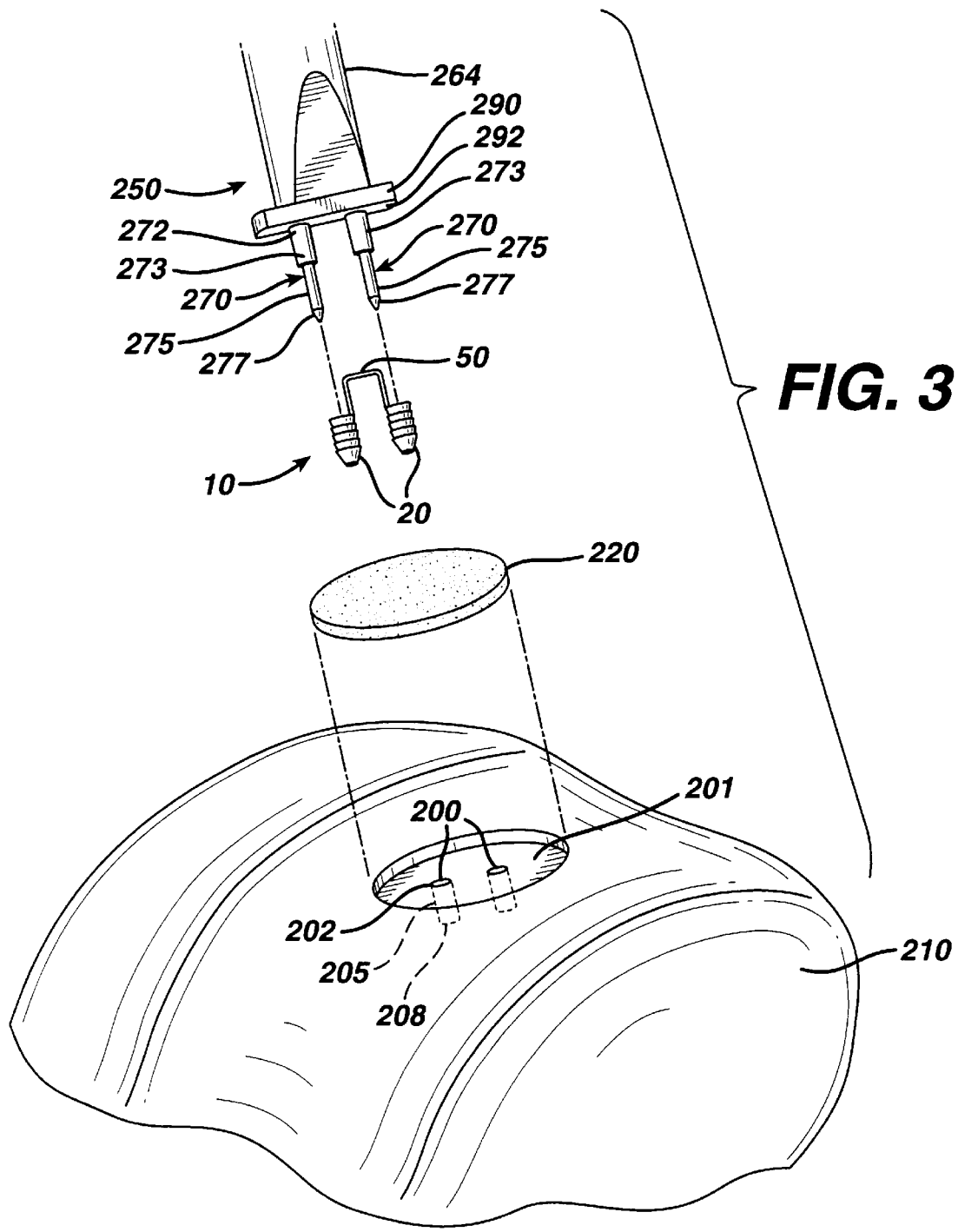
FIGS. 3–6 illustrate a surgical procedure for affixing a matrix to bone using the graft fixation device of the present invention.
Figure 4:
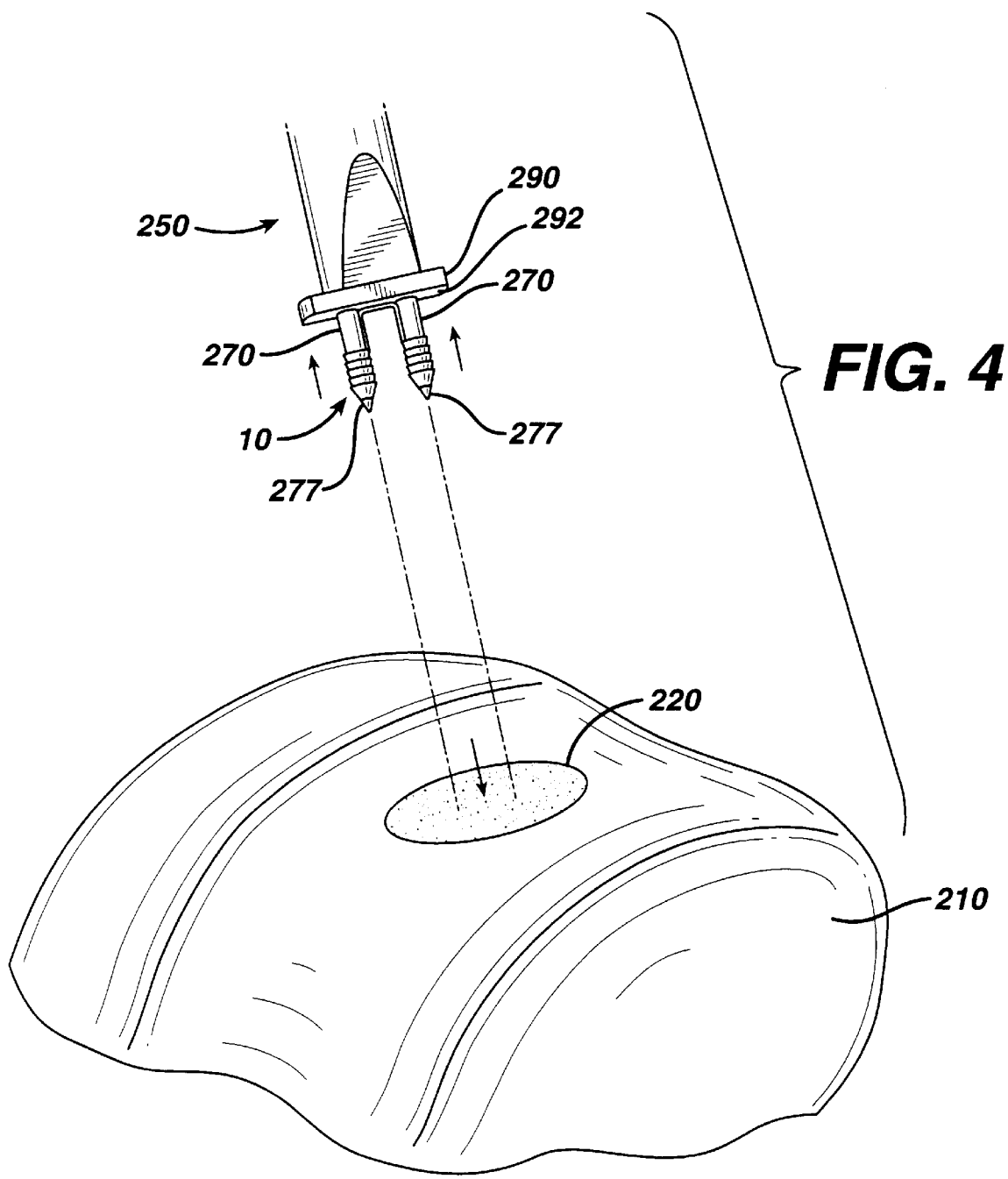
Figure 5:
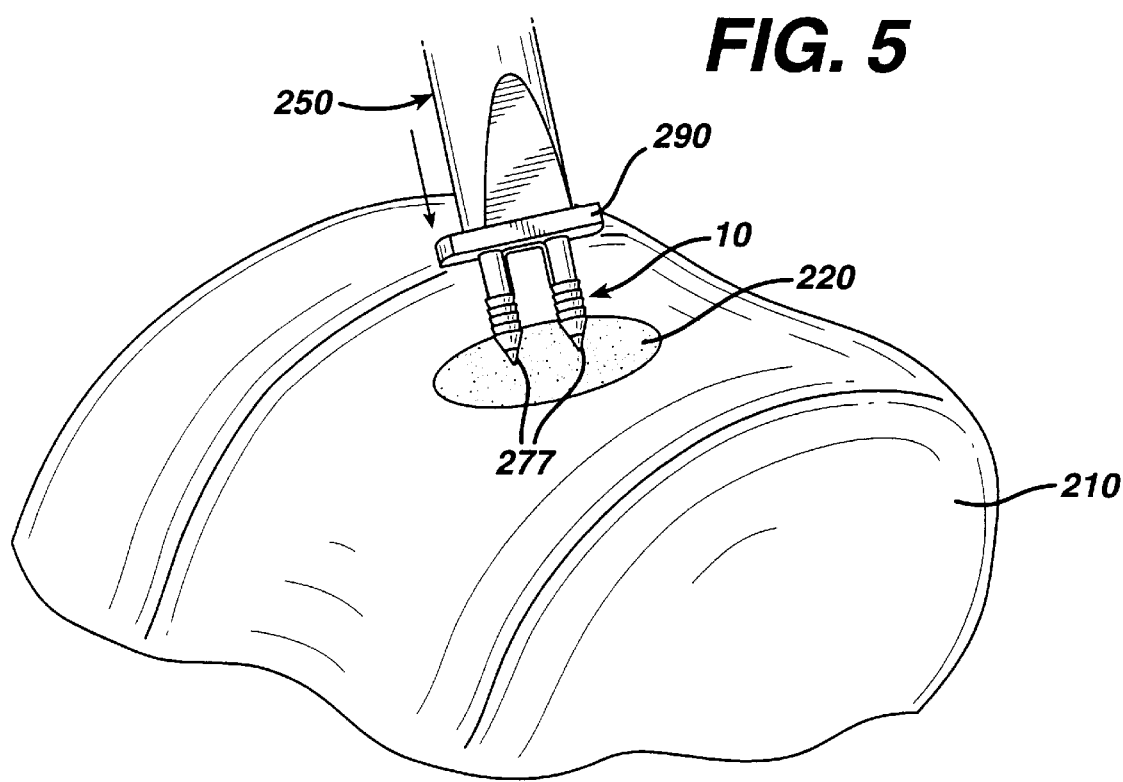
Figure 6:
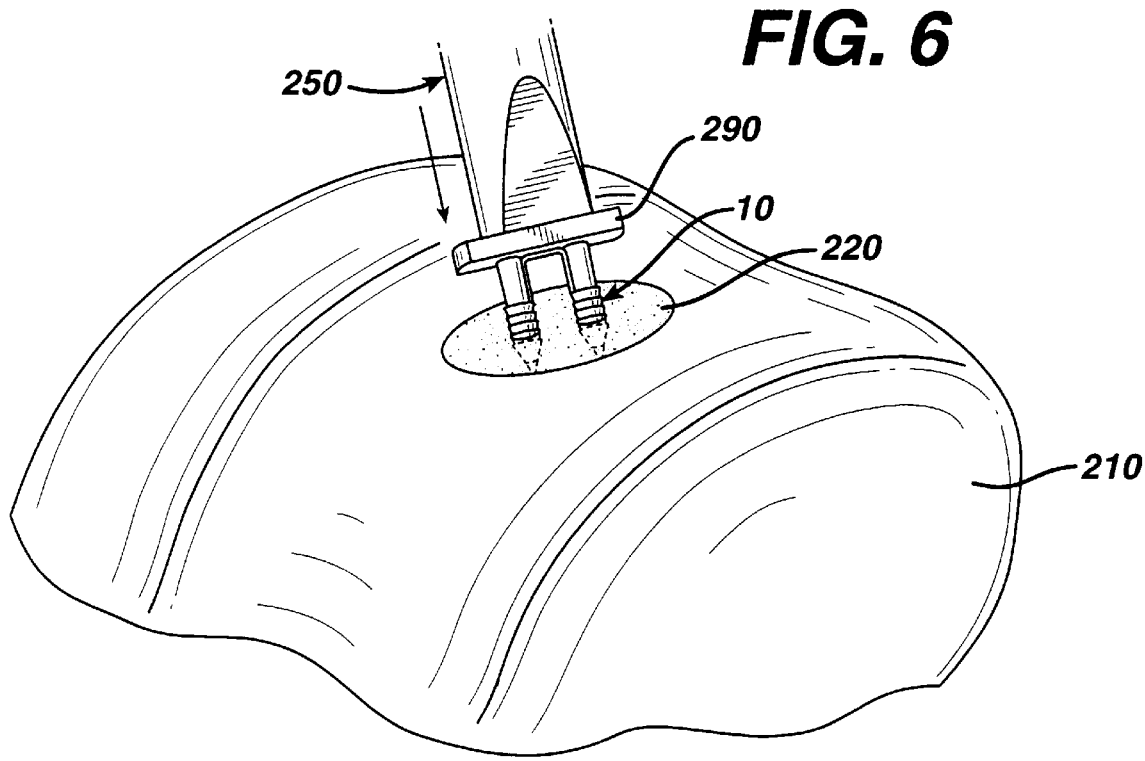
Figure 7:
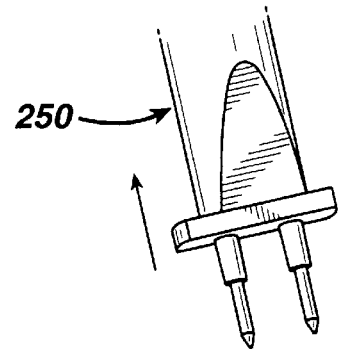
FIG. 7 is an illustration of a graft fixation device of the present invention after the implantation members have been implanted in bore holes in bone illustrating the device affixing a matrix securely to the surface of a bone.
Figure 7:
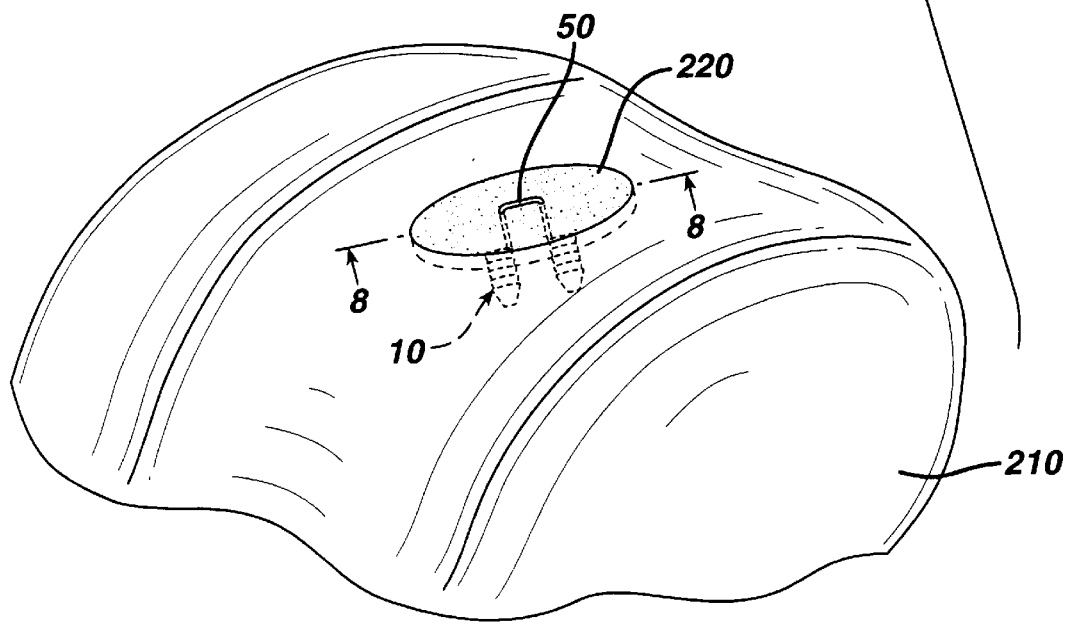
Figure 8:
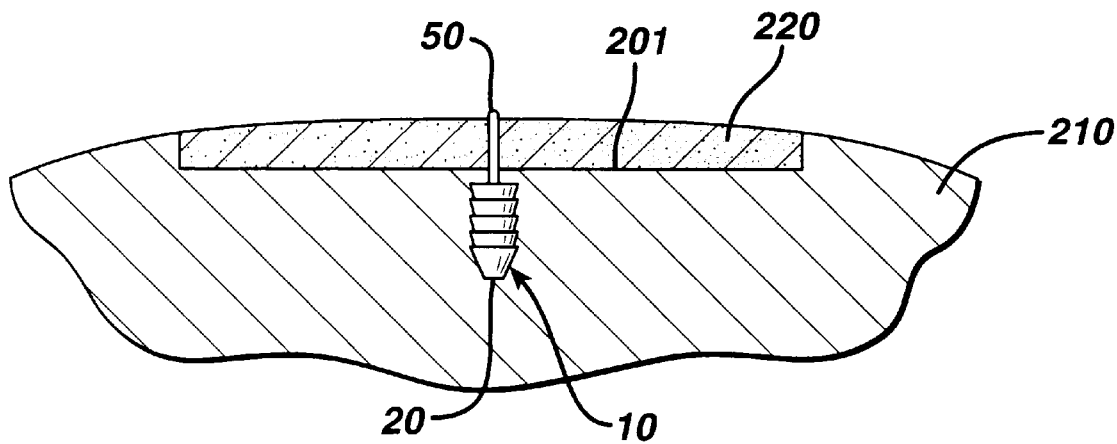
FIG. 8 is a cross-sectional view of the graft fixation device of FIG. 7 implanted in bone, and taken along View Line 8—8.
Figure 10:
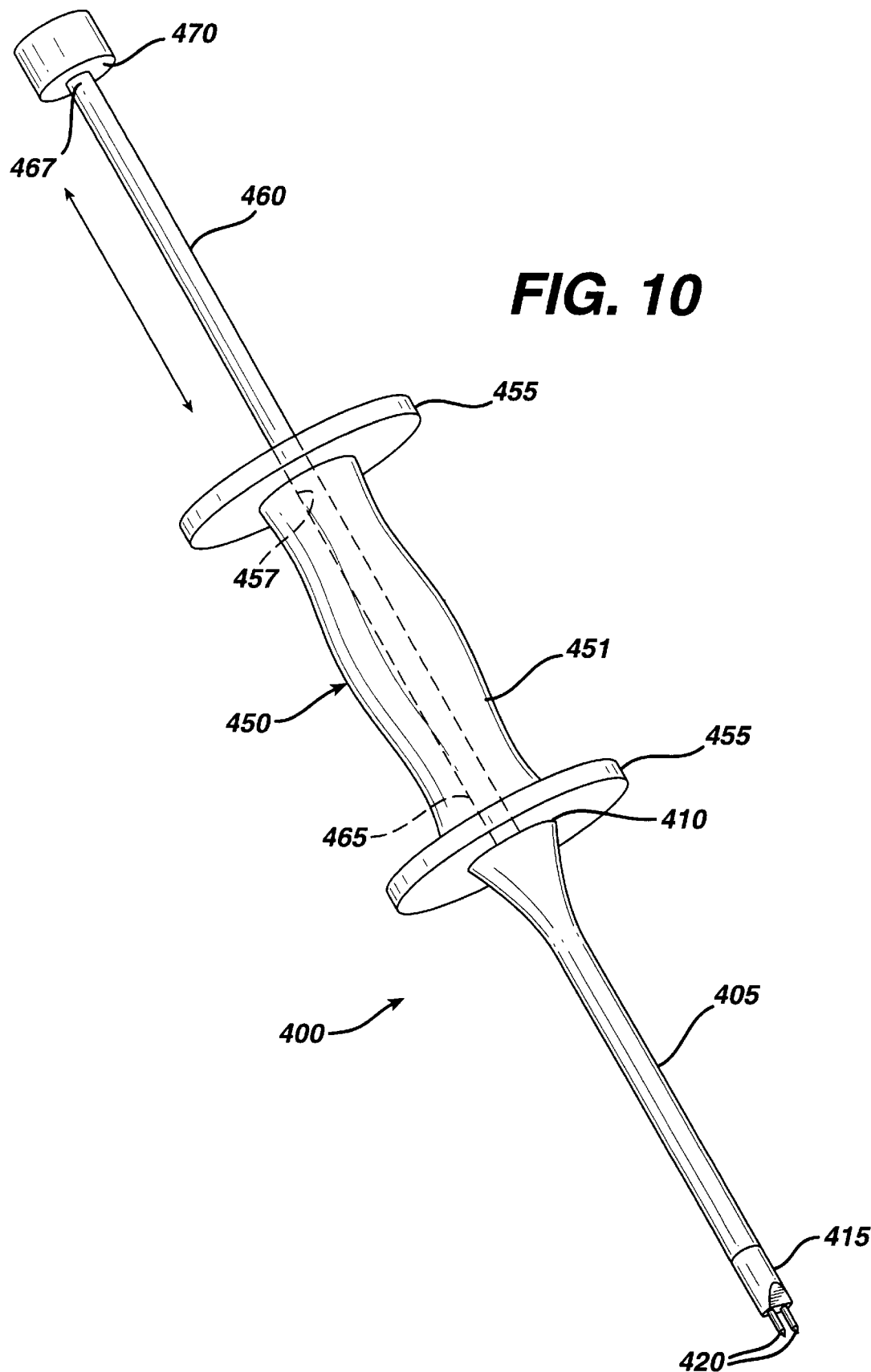
FIG. 10 is a perspective view of an instrument useful for making bore holes in bone into which the implantable members of the graft fixation devices of the present invention may be emplaced.
Figure 11:
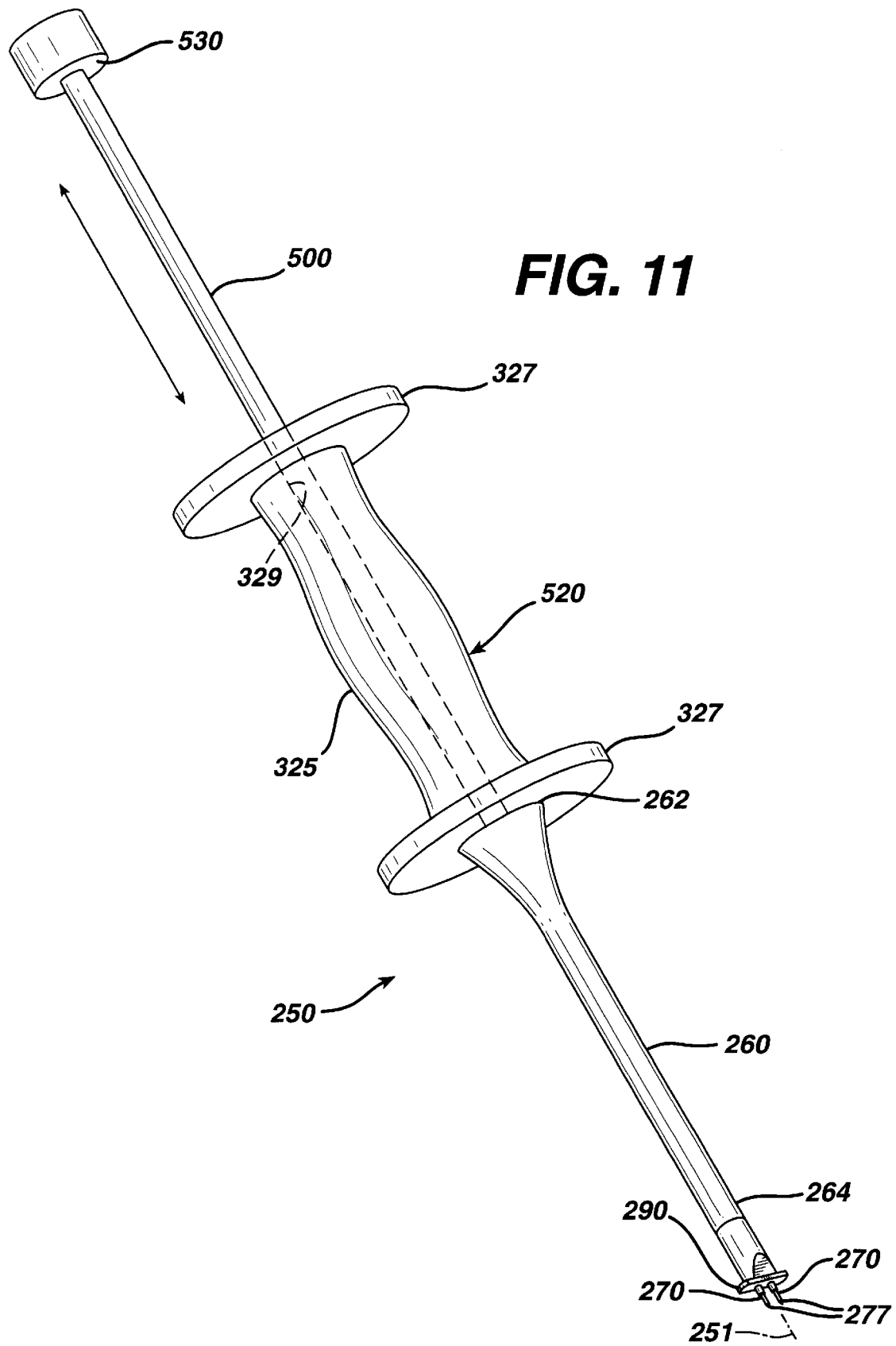
FIG. 11 is a perspective view of an instrument useful for implanting the device of the present invention into bore holes made in bone.

Referring now to FIGS. 3–8, the use of the graft fixation devices 10 of the present invention in a surgical procedure is illustrated. Referring first to FIG. 3, the initial step, prior to the installation of a matrix containing a tissue-engineered tissue using a graft fixation device 10 of the present invention, is to drill or "tap" two bore holes 200 into a bone 210, for example, subchondral bone in the knee joint. The bore holes 200 are seen to be cylindrical holes having a bottom 208 and an open top 202 and side walls 205. Optionally, the bore holes may be bone tunnels with a continuous passage and no bottom, or an open bottom. It is particularly preferred to tap the holes in the bone by using an instrument 400 as illustrated in FIG. 10 which has a proximal section conventionally referred to in this art as a "slap hammer" section. The term "tapping" or "tap" as used herein is defined to mean a procedure wherein the distal pointed prongs 420 extending from the distal end 415 of the shaft 405 of instrument 400 are located over a bone site, and the proximal end 410 of instrument 400 is tapped or hit with slidable hammer handle 450 (of the "slap hammer"), which slides on shaft 460 between proximal end 410 and proximal stop 470, to form the bone bore holes 200. The distal end 465 of shaft 460 is connected to proximal end 411. Proximal stop 470 is mounted to proximal end 467. Hammer handle 450 is seen to have grasping section 451, collars 455 and longitudinal passage 457. Those skilled in the art will appreciate that a similar pointed instrument may be used to "tap" in the bore holes into bone, that is, any instrument having a nail-like distal end. In addition, although not preferred, one bone bore hole at a time may be "tapped" in. If the surgeon decides to drill the bore holes into bone, any conventional surgical drilling apparatus may be used. After the bore holes 200 are formed into the bone 210, the matrix 220 containing tissue-engineering tissue is placed upon the bone surface 201 by the surgeon as seen in FIG. 4. Next, the graft fixation device 10 is mounted on to the insertion instrument 250. Insertion instrument 250, as illustrated in FIG. 11, is seen to be an elongated rod 260 having a proximal end 262 and a distal end 264. Mounted to the distal end 264 of the rod 260 is the depth stop 290. The depth stop 290 is seen to be a substantially rectangular member which is mounted perpendicular to the longitudinal axis 251 of the rod 260. Depth stop 290 is seen to have bottom 292. Extending distally from the bottom 292 of plate member 290 is a pair of parallel, spaced-apart, mounting prongs 270. The mounting prongs 270 are seen to be substantially rod-like members having distal pointed tips 277 and proximal ends 272. The prongs 270 are seen to have first section 273 and distal section 275. Section 273 is seen to have a greater cross-sectional dimension than distal section 275 such that the entire section 275 is insertable into passages 35 of members 20, while proximal section 273 is not insertable therein. Instrument 250 is also seen to have a "slap hammer section" consisting of proximal shaft 300 extending from proximal end 262, slidable hammer handle 320 (the "slap hammer") which is slidable upon shaft 300 between proximal end 262, and proximal stop 330. Hammer handle member 320 is seen to have grasping section 325, end collars 327 and longitudinal passage 329. The graft fixation device 10 is mounted to the insertion instrument 250 by sliding the implantation members 20 onto the prongs 270 such that the distal sections 275 of members 270 are engaged within the longitudinal passages 35 of members 20 and distal points 277 protrude beyond the end of distal endface surfaces 37. Then, as seen in FIGS. 5 and 6, the instrument 250 is manipulated such that the graft fixation device 10 is inserted through matrix 220 and into bone 210 by moving the implantation members 20 mounted on prongs 270 into the bore holes 200 such that the members 20 are engaged in the bore holes 200, and such that the tissue engagement section 55 of the retention member 50 engages the matrix 220 such that the matrix 220 is firmly engaged against the surface 201 of the bone 210. If desired, holes may be cut into matrix 220 prior to insertion of device 10. Then, as seen in FIG. 7, the insertion instrument 250 is withdrawn proximally causing the prongs 270 to be withdrawn from the passages 35 of the implantation members 20, thereby leaving the graft fixation device 10 engaged in the bone bore holes, and causing the matrix 220 to be maintained in engagement with the surface 201 of bone 210. The "slap hammer" section of instrument 250 may assist in removal of the prongs. A cross-sectional view illustrating the device 10 engaged in bone 210 while maintaining the matrix 220 on bone surface 201 is seen in FIG. 8.

Figure 12:
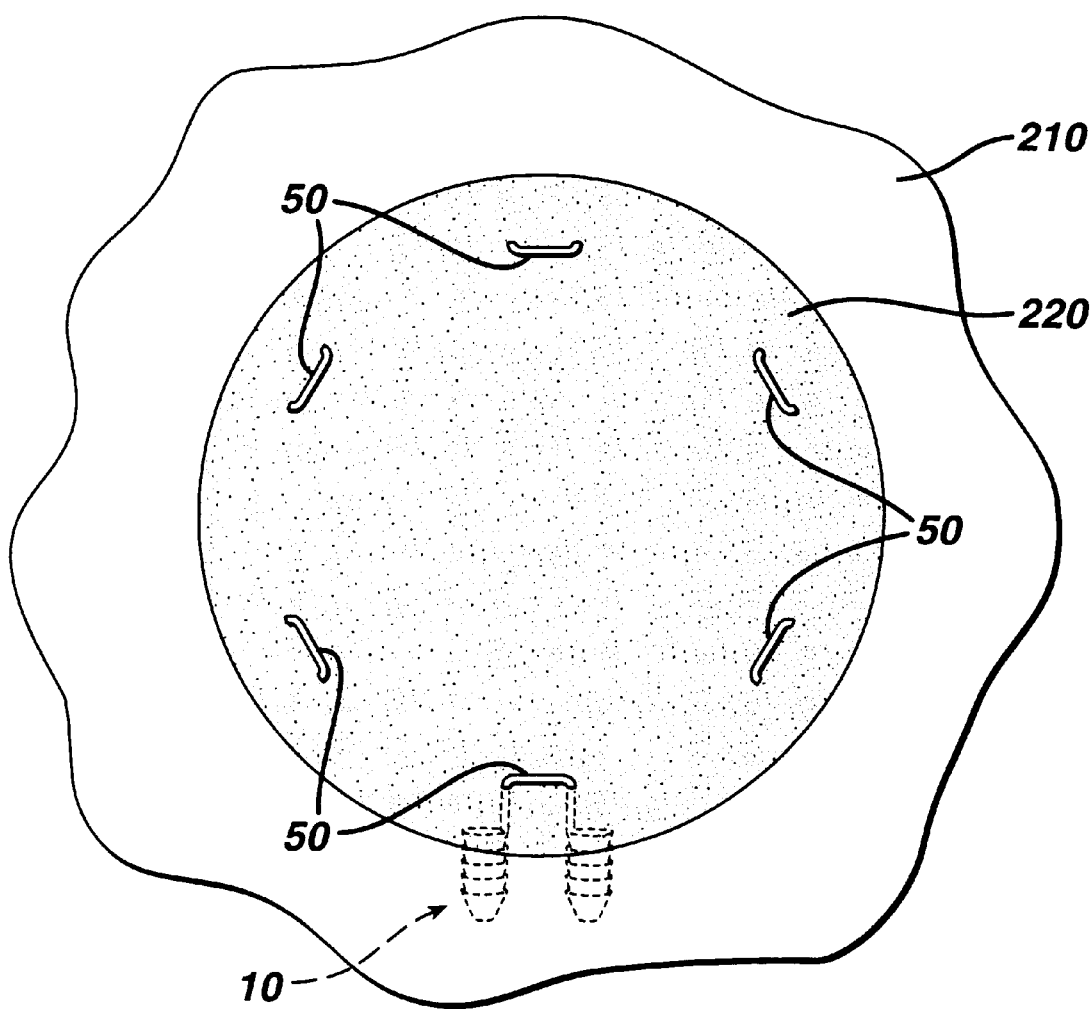
FIG. 12 is a view of a tissue engineered matrix secured to a bone with several graft fixation devices of the present invention.

FIG. 12 illustrates a matrix 220 mounted to bone surface 201 of bone 210 having multiple fixation devices of the present invention installed to secure the matrix 220. The number, anatomical location and orientation of fixation devices 10 necessary to provide sufficiently effective fixation will vary with the size and type of implant or matrix, the type of tissue, the age of the patient, the size of the patient's defect, the size of the fixation devices, the material of construction of the fixation devices, the load on the tissue at the repair site, etc.

Those skilled in the art will appreciate that the size of the fixation devices of the present invention will vary in accordance with a number of variables including the specific design of the device, the materials of construction, the specific application for the devices, the type of surgical procedure, etc. Similarly, the size of the matrices fixated with these devices will similarly vary. The Figures which are part of this specification are merely schematic and illustrative of the device and method of the present invention; the actual dimensions of the devices and matrices may vary in practice.

The following example is illustrative of the principles and practice of the present invention although not limited thereto.

EXAMPLE

Six sheep were prepared for a surgical procedure using standard aseptic surgical techniques including the use of fully sterilized instruments and equipment, and conventional anesthesia procedures and protocols. The surgeon then created 7 mm diameter chondral (full thickness cartilage) defects on a weight-bearing area of the medial femoral condyle and in the trochlear groove in the right stifle (knee) in each of the six skeletally mature sheep. Defects were created using a specialized drill with a depth-stop to prevent subchondral bone exposure or penetration. The base surfaces of all the defects were then microfractured with a specialized micropick tool to provide access for cellular migration. The subjects were then separated into three groups of two subjects each:

Group 1: defect filled with a collagen matrix, fixed with the graft fixation device of the present invention.
Group 2: defect filled with a collagen matrix, fixed with 9-0 absorbable Vicryl™ suture (interrupted stitch technique, approximately 12 strands per matrix).
Group 3: unfilled defect (control group).
Both defects in a given stifle received the same treatment or served as controls.

For the two sheep in Group 1, after a defect had been created and microfractured, a punch tool 400 was used to create the two requisite bore holes in the subchondral bone to receive one graft fixation device of the present invention. Only one polydioxanone device (4 mm tip-to-tip distance) was used to attach each matrix. To create the bore holes, the punch tool was centered in the defect, oriented in the sagittal plane, and hit or "tapped" with a slap hammer repeatedly until it penetrated several millimeters into the subchondral bone. Next, a 7 mm diameter circular collagen matrix, saturated with saline, was placed in the defect and then blotted dry to remove excess saline. When the inserter tool 250 was loaded with the graft fixation device 10 of the present invention, the device and inserter tool were centered above the matrix and oriented in the sagittal plane. The surgeon then located the previously created bore holes by slowly advancing the distal tips of the inserter through the matrix. Once the surgeon located the holes with the inserter tips, a hammer was used to fully advance the inserter tool (and implantation members 20 of the fixation device 10) through the matrix and into the subchondral bone. The inserter tool had a depth stop to prevent the implantation members 20 from being inserted too deeply, thereby assuring the proper placement of the implantation members through the matrix. The insertion was completed when the connecting retention member between the two implantation members initially started to compress the collagen matrix, thereby indicating secure fixation with the underlying subchondral bone. After the two defects in a given stifle had each been repaired with a matrix and fixation device, the stifle was closed and the sheep was allowed to recover. It was noted by the surgeon that it took approximately one minute to attach a matrix with a fixation device of the present invention (Group 1), versus approximately 15 minutes to attach a matrix with suture alone and the requisite suture manipulation and knot tying (Group 2).

Two weeks after the surgeries were completed, the knee joints were surgically opened for examination. Gross macroscopic assessment of the joints demonstrated that all four matrices held by the graft fixation device of the present invention were fully intact. However, all four matrices held by sutures alone were only partially intact with, on average, approximately 30% of the sutures broken on any given matrix.

Figure 9:
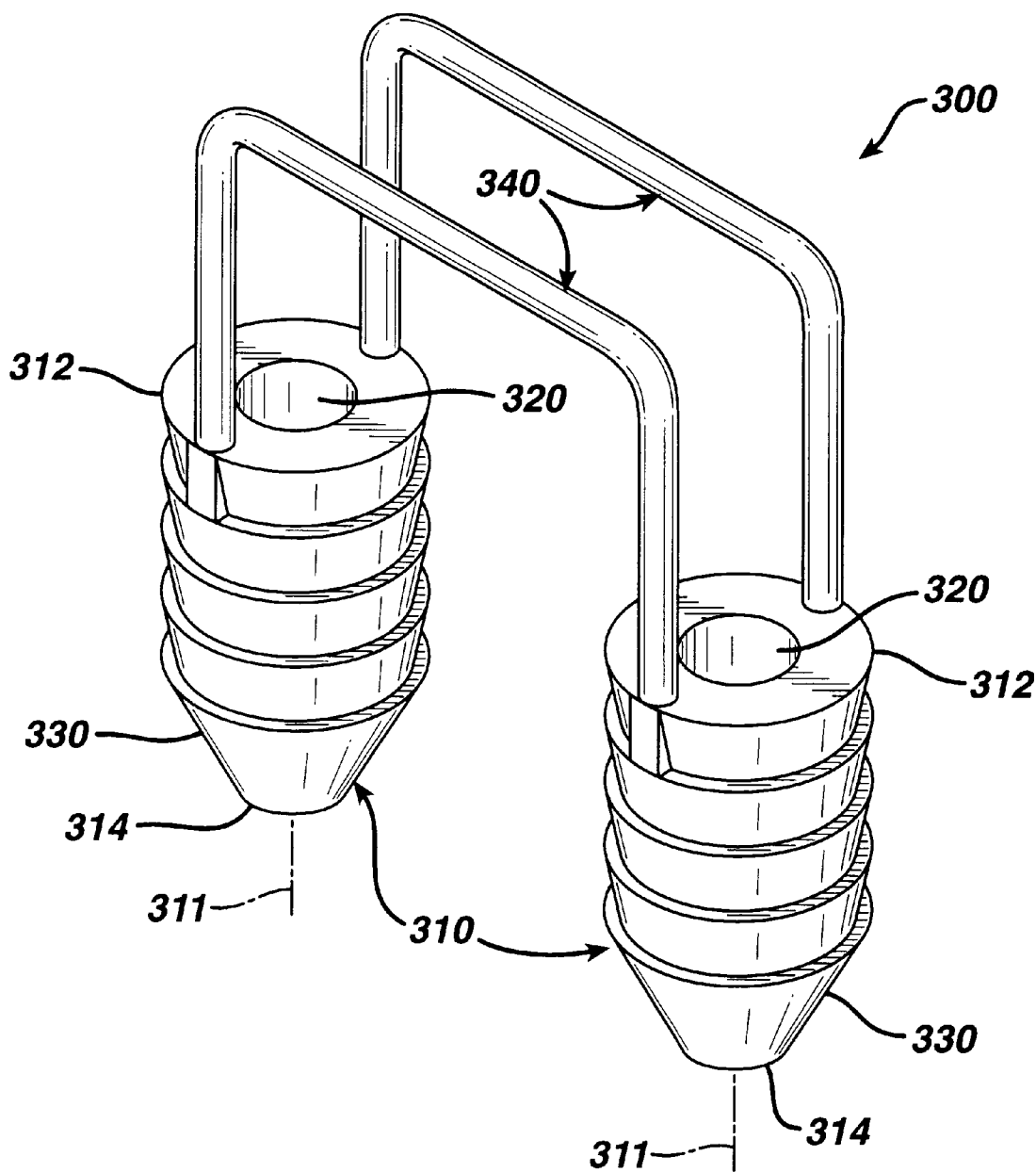
FIG. 9 is an alternative embodiment of a graft fixation device of the present invention having two connecting members.

Another embodiment of the fixation device of the present invention having multiple retention members is seen in FIG. 9. The device 300 is seen to have a pair of implantation members 310. The implantation members 310 are substantially cylindrical members having longitudinal axis 311, distal ends 314 and proximal ends 312. Each implantation member 310 is seen to have a longitudinal passage 320. The members 310 are seen to have a distal frustoconical end 330, outer surface 350, and ridges 355 extending outward from surface 350. The members 310 are seen to be connected by a pair of retention members 340, having first and second ends 342 and 344 respectively.

The fixation devices 10, and method of using such devices, of the present invention have many advantages. The advantages include providing a fast and routine way to fixate a matrix of tissue engineered tissue or other tissue. The fixation devices 10, because they eliminate the need for suture knot tying, can be utilized in arthroscopic surgical procedures that require a minimum of surgical incision and thus greatly reduce patient morbidity. In addition, the fixation devices 10 have been demonstrated to provide excellent matrix fixation without damaging the surrounding normal cartilaginous tissue, unlike the conventional fixation of chondral defect matrices with traditional suture that must be passed through (and thus damage) the surrounding tissue.

Although this invention has been shown and described with respect to detailed embodiments thereof, it will be understood by those skilled in the art that various changes in form and detail may be made without departing from the spirit and scope of the claimed invention.

I claim:

1. A method of mounting a matrix to tissue, comprising the steps of:

providing a graft fixation device, said device comprising:

a first implantation member, said implantation member having a longitudinal axis, a proximal end, a distal end, an outer surface, and a longitudinal passage therethrough;

a second implantation member, said implantation member having a longitudinal axis, a proximal end, a distal end, an outer surface, and a longitudinal passage therethrough;

a proximal annular face on the proximal ends of the first and second implantation members surrounding the longitudinal passage; and, a connecting member connecting the first and second implantation members, the connecting member having a central section, a first end extending from the first implantation member and a second end extending from the second implantation member;

forming a pair of spaced apart bore holes in bone;

mounting the device to an insertion instrument having a pair of spaced apart prongs, said prongs having distal ends, such that the prongs are contained within the passages of the implant members and the distal ends extend beyond the distal ends of the implant members;

placing a matrix onto the surface of the bone over the bore holes;

and inserting the implantation members through the matrix and into the bore holes, thereby securing the matrix to the bone.

2. The method of claim 1, wherein the implantation members have a series of ridges extending from the outer surfaces thereof.

3. The method of claim 1, wherein the connecting member is shaped into a configuration having a central section and rod members, wherein the rod members are substantially parallel to the longitudinal axes of the implantation members, and the central section is substantially perpendicular to the rod members.

4. The method of claim 1, wherein the connecting member has a semi-circular configuration.

5. The method of claim wherein the implantation members additionally comprise a frustoconical end extending from the distal end of the first implantation member and the distal end of the second implantation member.

6. The method of claim 1 wherein the implantation members have a cylindrical configuration.

7. The method of claim 1, wherein each prong additionally comprises a point extending from the distal end.

8. The method of claim 1, wherein each prong comprises a distal section having a cross-section and a proximal section having a cross-section, wherein the area of the cross-section of the proximal section is greater than the area of the distal cross-section.

9. The method of claim 1, wherein each prong has a circular cross-section.

* * * * *

UNITED STATES PATENT AND TRADEMARK OFFICE
CERTIFICATE OF CORRECTION

PATENT NO. : 6,179,840 B1
DATED : January 30, 2001
INVENTOR(S) : Steven M. Bowman It is certified that error appears in the above-identified patent and that said Letters Patent is hereby corrected as shown below:

<u>Column 8, claim 5,</u>
Line 21, should read claim -- 1 --

Signed and Sealed this

Twenty-fifth Day of December, 2001

Attest:

Attesting Officer

JAMES E. ROGAN
Director of the United States Patent and Trademark Office